(12) United States Patent
Arkles et al.

(10) Patent No.: US 10,487,242 B2
(45) Date of Patent: Nov. 26, 2019

(54) STABILIZED SOLUTIONS OF ALKYLALKOXYSILANE HYDROLYSATES AND FLEXIBLE FILMS FORMED THEREOF

(71) Applicant: Gelest Technologies, Inc., Morrisville, PA (US)

(72) Inventors: Barry C. Arkles, Pipersville, PA (US); Jonathan D. Goff, Philadelphia, PA (US)

(73) Assignee: Gelest Technologies, Inc., Morrisville, PA (US)

(*) Notice: Subject to any disclaimer, the term of this patent is extended or adjusted under 35 U.S.C. 154(b) by 0 days.

(21) Appl. No.: 15/670,045

(22) Filed: Aug. 7, 2017

(65) Prior Publication Data

US 2018/0044550 A1 Feb. 15, 2018

Related U.S. Application Data

(60) Provisional application No. 62/373,745, filed on Aug. 11, 2016.

(51) Int. Cl.

| | | |
|---|---|---|
| *A61K 31/74* | (2006.01) |
| *C09D 183/08* | (2006.01) |
| *A61K 8/06* | (2006.01) |
| *A61K 8/37* | (2006.01) |
| *A61K 8/58* | (2006.01) |
| *A61K 8/898* | (2006.01) |
| *A61Q 5/00* | (2006.01) |
| *C04B 41/00* | (2006.01) |
| *C04B 41/49* | (2006.01) |
| *C04B 41/64* | (2006.01) |
| *C09D 5/16* | (2006.01) |
| *A61Q 5/12* | (2006.01) |
| *B05D 5/08* | (2006.01) |
| *C04B 103/00* | (2006.01) |
| *C08G 77/26* | (2006.01) |
| *C08G 77/04* | (2006.01) |
| *C08G 77/00* | (2006.01) |

(52) U.S. Cl.
CPC .............. *C09D 183/08* (2013.01); *A61K 8/06* (2013.01); *A61K 8/37* (2013.01); *A61K 8/585* (2013.01); *A61K 8/898* (2013.01); *A61Q 5/00* (2013.01); *A61Q 5/12* (2013.01); *C04B 41/009* (2013.01); *C04B 41/4922* (2013.01); *C04B 41/4961* (2013.01); *C04B 41/64* (2013.01); *C09D 5/1675* (2013.01); *A61K 2800/52* (2013.01); *B05D 5/08* (2013.01); *C04B 2103/0052* (2013.01); *C08G 77/045* (2013.01); *C08G 77/26* (2013.01); *C08G 77/80* (2013.01)

(58) Field of Classification Search
None
See application file for complete search history.

(56) References Cited

U.S. PATENT DOCUMENTS

| | | | |
|---|---|---|---|
| 4,648,804 A | 3/1987 | Jones et al. | |
| 4,661,551 A | 4/1987 | Mayer et al. | |
| 4,708,743 A | 11/1987 | Schmidt | |
| 5,037,873 A * | 8/1991 | Heaton | ............... C04B 41/4922 524/267 |
| 5,051,129 A * | 9/1991 | Cuthbert | ............... C04B 41/009 106/2 |
| 6,610,782 B1 | 8/2003 | Weiland | |
| 2003/0212228 A1 | 11/2003 | Dai et al. | |
| 2013/0167860 A1 | 7/2013 | Singer et al. | |

FOREIGN PATENT DOCUMENTS

| | | | |
|---|---|---|---|
| CN | 104559770 A | 4/2015 | |
| EP | 0552874 A2 * | 7/1993 | ........... C04B 1/4966 |
| EP | 0616990 A1 | 9/1994 | |
| EP | 1136494 A2 * | 9/2001 | ........... C07F 7/0874 |
| EP | 1 136 494 A3 | 12/2001 | |
| EP | 1217119 A1 | 6/2002 | |
| EP | 1736139 A1 | 12/2006 | |
| WO | 2008134243 A1 | 11/2008 | |
| WO | 2010108781 A1 | 9/2010 | |

OTHER PUBLICATIONS

Arkles et al., "Factors contributing to the stability of alkoxysilanes in aqueous solution," Silanes and Other Coupling Agents, pp. 91-104, (1992).
Arkles et al., "Factors contributing to the stability of alkoxysilanes in aqueous solution," Journal of Adhesion Science and Technology, vol. 6, No. 1, pp. 193-206, (1992). Abstract Only.
Int'l Search Report and Written Opinion dated Nov. 10, 2017 in Int'l Application No. PCT/US2017/046433.

* cited by examiner

*Primary Examiner* — Susan T Tran
(74) *Attorney, Agent, or Firm* — Panitch Schwarze Belisario & Nadel LLP

(57) ABSTRACT

A stabilized mixture containing an alkyltrialkoxysilane hydrolysate solution and an amine functional silicone emulsion is provided. The stabilized mixture may be utilized in a masonry treatment product or a cellulosic or wood treatment product, such as to provide waterproofing properties, or in a hair care treatment product for improving hair combability. A method of preparing the mixture involves hydrolyzing an alkoxysilane to form an aqueous solution containing alkylsilanetriols and/or oligomeric alkylsilanetriol condensates; and stabilizing the solution by adding an amine functional silicone.

18 Claims, No Drawings

STABILIZED SOLUTIONS OF ALKYLALKOXYSILANE HYDROLYSATES AND FLEXIBLE FILMS FORMED THEREOF

CROSS-REFERENCE TO RELATED APPLICATIONS

This application claims priority from U.S. Provisional Application No. 62/373,745, filed Aug. 11, 2016, the disclosure of which is herein incorporated by reference.

BACKGROUND OF THE INVENTION

The use of alkyltrialkoxysilanes and their hydrolysates as surface treatments in applications such as clear penetrating water-repellents for masonry is well-established. In other applications, penetration of the substrate must be accompanied by the ability to form a film on the surface substrate. This result can be achieved with relative ease for fixed high modulus "stiff" substrates. In contrast, flexible substrates, such as metallized food packaging, cellulosic substrates including wood and paper, and personal care products with substantivity on hair and skin, are more difficult since the condensation and polymerization products of alkyltrialkoxysilanes (which may be referred to as silsesquioxanes or T resins) are stiff and generally cannot withstand flexure. Even more extreme demands are found for outdoor wood and cosmetic applications, such as hair care formulations, where adhesion permanence and substantivity is defined in terms of rain or wash resistance. This requires formation of water-resistant, flexible, tenacious films with appropriate sensory properties. Compositions useful for this purpose may be generally classified as either water-borne or non-waterborne. The performance, particularly silane penetration of porous substrates and, consequently, resistance to ions (salt), detergents and water transport is generally superior in non-waterborne systems. However, safety and environmental considerations favor the use of water-borne systems.

An intrinsic element of alkylalkoxysilane chemistry generally limits the stability of these materials in aqueous systems. Specifically, the alkoxy group hydrolyzes in water to form an active silanol species. This species can react with the surface hydroxyls of the siliceous substrates, rendering them hydrophobic, or they can react with themselves, forming silsesquioxanes which precipitate out of solution. General considerations of the factors affecting stability of alkoxysilanes in aqueous solution have been reviewed (B. Arkles et al, *J. Adhes. Sci & Technol,* 6(1), 193 (1992)).

Two approaches are generally employed in current commercial formulation technology. The first approach is to form oligomeric alkylalkoxysilanes and then to emulsify these systems. One example is for mixed alkylalkoxysiloxane oligomers. The oligomeric nature of these materials tends to prevent hydrolysis of the silanes under neutral conditions. On the other hand, the increase in molecular size prohibits deep penetration into submicron pores in siliceous substrates. Another example (see U.S. Pat. No. 4,661,551) are silsesquioxanes generated from mixed hydrolysates of aminoethylaminopropyltrialkoxysilane and alkyltrialkoxysilanes. These high amine-content materials generally discolor substrates and have generally low penetrations since the high temperature hydrolysis results in high molecular weight.

In the second approach (see U.S. Pat. No. 4,648,804), long chain alkyltriethoxysilanes, e.g., octyltriethoxysilane, are stabilized as monomers in a micelle or emulsion form. When the micelle or emulsion breaks down on contact with a masonry substrate, the octyltriethoxysilane is no longer stable and reacts with the substrate. This approach has the same deficiency as the oligomeric silanes in that the long alkyl chain precludes penetration of the silane. Comparative tests of these products under standard NCHR 244 tests indicate that they generally penetrate only $3/16''$ compared to at least twice the penetration for systems such as alcohol solutions of isobutyltrimethoxysilane. In a similar approach (see U.S. Pat. No. 6,610,782), a binary emulsion is formed from a combination of an hydrolyzable silane, more specifically an alkyltrialkoxysilane or low molecular weight alkyltrialkoxysilane oligomeric hydrolysate, a low molecular weight silicone, an aminofunctional fluid and an aminofunctional silane in water.

A third approach is exemplified in EP 1 136 494 A3, in which the transesterification of alkyltrialkoxysilanes with polyhydroxyl compounds, usually with the concomitant removal of lower alcohols in aqueous solution, is disclosed.

Still another approach is to stabilize the reactive intermediate, the silanetriol, in aqueous systems. Stabilizing the triol maintains the low molecular weight needed to penetrate the various micro-porous substrates. However, prior work has not been able to provide stable solutions of alkylsilanetriols suitable for commercial water repellents. While U.S. Pat. No. 4,708,743 describes methods for producing solutions of propylsilanetriol that are stable for up to 24 hours, this necessitates on-site mixing, and practical experience indicates that the solutions are usually not stable for more than six hours. Aged solutions have silsesquioxane materials which can stain masonry. Nevertheless, penetration of the propylsilanetriol is intermediate between emulsions of alkoxysilanes and alcohol solutions of alkoxysilanes. Accordingly, stable solutions of alkylsilanetriols for commercial water repellants would be desirable.

BRIEF SUMMARY OF THE INVENTION

In one embodiment, the invention provides a stabilized mixture comprising an alkyltrialkoxysilane hydrolysate solution and an amine functional silicone emulsion.

DETAILED DESCRIPTION OF THE INVENTION

The present invention provides stable mixtures containing alkylsilanetriols, alkyltrialkoxysilane hydrolysates which may alternatively be considered oligomeric alkylsilanetriol condensates, and amine functional silicone emulsions. The solutions of alkyltrialkoxysilane hydrolysates are stable and preferably contain high contents of alkylsilanetriols and low molecular weight alkylsilanetriol condensation products having two to three silicon atoms. The alkylsilanetriols and low molecular weight condensation products are formed by hydrolysis of alkyltrialkoxysilanes, preferably alkyltriethoxysilanes, in moderately dilute aqueous systems. Preferably, the alkyl group in the alkyltrialkoxysilane contains about one to ten carbon atoms, more preferably two to about eight carbon atoms, and the alkoxy group contains about one to four carbon atoms. The alcohol byproduct formed by hydrolysis may remain in the solution or may be removed by azeotropic distillation.

The alkylsilanetriol or oligomeric alkylsilanetriol condensate solution is then stabilized by addition, preferably in emulsion form, of a high molecular weight amine functional polysiloxane (silicone), preferably containing alkoxy groups. It is believed that the ability of the non-aqueous phase of the emulsion to absorb the relatively hydrophobic silanol species and the ability of the amine to form ionic silanolate species both contribute to the stabilization.

The inventive compositions demonstrate substantially greater penetration of porous substrates which anchor polymeric films on the surface of the substrate. Masonry and concrete treated with the compositions of this invention demonstrate greater penetration than previously reported waterborne silanes. For example, specimens of yellow pine treated with the inventive compositions demonstrated hydrophobic behavior after over 100 hours of water spray. Similarly, the stabilized solutions of alkylalkoxysilanetriols penetrate the cuticle layer of hair, while concomitantly condensing to form a flexible compliant film, providing desirable sensory attributes such as shine, feel and combability on a semi-permanent basis.

While a portion of the silanetriols may condense to form low molecular weight siloxanes with two to three silicon atoms, the essential part of this invention is that the silanetriols and any siloxanes formed are maintained as low molecular weight species during storage and application, allowing them to diffuse and penetrate porous substrates before condensing to form polysilsesquioxanes. On drying, the silanol species undergo condensation and polymerization to form the polysilsesquioxanes. In the case of siliceous substrates, surface silanols provide condensation sites.

The compositions of the invention have even greater utility on flexible substrates, such as packaging and hair, where they demonstrate the ability to withstand flexure and aggressive washing. The resulting treated hair exhibits improved "combability," that is, the ability to more easily brush or comb the hair without tangling or knotting. The success of the approach in hair is believed to be associated with both the interaction of silanol groups with amino acid residues on the cuticle surfaces and the penetration between the cells in the cuticle layer. In the case of hair treatment, it should be noted that the sensory factors, feel and gloss, are benefits of this technology that are related to but can be distinguished from film-formation and hydrophobicity.

The invention also includes masonry, cellulosic, wood, and hair care treatment products containing the inventive material. Methods of waterproofing masonry, cellulosic, and wood objects and for treating hair involve applying the inventive mixtures to the desired object or hair.

A method for preparing the inventive mixtures is also provided. The method involves first hydrolyzing an alkyltrialkoxysilane having an alkyl chain length of ten or less in water utilizing a small portion of organic or mineral acid. Shortly after the hydrolysis is complete, the method involves neutralizing the solution and adding a small portion of an aminofunctional silicone. The formation of the alkylsilanetriol is usually evidenced by the initial two phase mixture of water-insoluble alkyltriethoxysilane and water which becomes a single phase as the water-soluble silanol species, alkylsilanetriol and oligomeric alkylsilanetriol condensates are formed. The amino functional silicone stabilizes the silanol species, presumably by forming a silanolate anion and a cationic amine. Optionally, the alcohol byproduct formed by hydrolysis may be removed by azeotropic distillation, for example. The stabilized silanetriol solution may be used in immediately in this form. Alternatively, the emulsion stabilized silanetriol solution is stable and can be allowed to age. Compositions formed in this manner have demonstrated stability for greater than 2 years. The inventive mixtures contrast with those described in U.S. Pat. No. 6,610,782, in which efforts are made to preserve the alkoxy groups on the silane constituents. It is further believed that the smaller molecular dimensions of alkylsilanetriols compared to alkyltrialkoxysilanes is of great benefit in penetration of submicron structures. Unstabilized alkylsilanetriols polymerize in hours to form polysilsesquioxanes which typically precipitate from solutions.

In a further embodiment, a hydrophilic material, preferably hydroxyethylmethacrylate, is added to the mixture. The hydrophilic material aids in penetration and ultimately affords a superior hydrophobic coating. This is a particularly unexpected result since a hydrophilic material is facilitating a hydrophobic coating. While not wishing to be bound by theory, it is believed that the hydroxyethylmethacrylate behaves as a surfactant in dilute solution, but on drying forms a less hydrophilic ester with the silanetriols facilitating film formation.

In a further embodiment of the invention, the emulsion may be further stabilized by adding small amounts of polydialkylsiloxane fluids that are compatible with the alkylsilanetriol and the aminofunctional silicone. Polymethylethylsiloxane and polydiethylsiloxane are exemplary.

It is also within the scope of the invention to incorporate more than one silanol species into a composition for modification of the resulting films. For example, lower alkylsilanetriols such as ethylsilanetriol form harder (less flexible) films than those from higher branched silanes such as isooctylsilanetriol. Intermediate flexibility can be achieved with a mixture of silanetriols. A secondary characteristic, such as gloss or shine, can be achieved by forming a material such as phenethylsilanetriol in the composition. Alternately, gloss may be achieved by adding a low molecular weight silanol-terminated diphenylsiloxane-dimethylsiloxane copolymer.

The invention will now be described in connection with the following, non-limiting examples.

Synthesis Example 1

A 3 neck flask equipped with a moderate speed (50-500 rpm) stirrer was charged with 1700 mL of deionized water and 4 mL of acetic acid. Propyltriethoxysilane (160 mL) was added rapidly through an addition funnel. Initially, the mixture had two phases, but in 3-5 hours, the mixture became a single homogeneous phase. As soon as the solution was homogeneous, 80 mL of 1M sodium bicarbonate solution was added. After the neutralization was complete, 65 grams of a diamine functional silicone emulsion containing 50% solids, having an amine equivalent 0.45 mEq/g and sold by Momentive Inc. under the trade name SM2159, was added to the mixture with low speed (<50 rpm) agitation. The mixture was allowed to age at room temperature for at least 24 hours and then 100 mL of hydroxyethylmethacrylate were added.

Application Example A

The product of Example 1 was applied by brushing (or spraying) the mixture onto a cured concrete test block which had been aged for at least 2 months. After 72 hours, the concrete block was split and immersed in water. The concrete was hydrophobic to a depth of ⅜".

Synthesis Example 2

This Example is similar to that of Example 1 but is a higher solids version. According to the method of Example 1, the following components were added: 1700 mL deionized water, 320 mL propyltriethoxysilane, 8 mL acetic acid, 160 mL 1 M NaHCO$_3$, and 130 mL SM2159, but the hydroxyethylmethacrylate was not added.

Application Example B

The product of Example 2 was applied to hair specimens, worked in for approximately 2 minutes, and then rinsed. The hair specimens exhibited a smooth feeling and shine. The hair specimens were shampooed twenty times with retention of both smooth feeling and shine.

Synthesis Example 3

Example 1 was repeated, except that octyltriethoxysilane was substituted for propyltriethoxysilane.

Synthesis Example 4

Example 1 was repeated, except that Wacker Silicones BS1306 was substituted for Momentive SM2159.

Synthesis Example 5

Example 1 was repeated, except that 1 wt % of Gelest PDS-1615, a low molecular weight (15-20 mol % diphenylsiloxane)-(80-85 mol % dimethylsiloxane) copolymer, was added to increase gloss.

Synthesis Example 6

Example 1 was repeated, except that 5 wt % of Gelest PDS-1615, a low molecular weight (15-20 mol % diphenylsiloxane)-(80-85 mol % dimethylsiloxane) copolymer, was added to increase gloss.

Synthesis Example 7

Example 3 was repeated, except that 1 wt % of Gelest PDS-1615, a low molecular weight (15-20 mol % diphenylsiloxane)-(80-85 mol % dimethylsiloxane) copolymer, was added to increase gloss.

Synthesis Example 8

Example 3 was repeated, except that 5 wt % of Gelest PDS-1615, a low molecular weight (15-20 mol % diphenylsiloxane)-(80-85 mol % dimethylsiloxane) copolymer, was added to increase gloss.

Synthesis Example 9

Example 1 was repeated, except that 5 wt % of Gelest DE-15 polydiethylsiloxane, a low molecular weight siloxane, was added to reduce "tack" and improve combability.

Synthesis Example 10

Example 1 was repeated, except that 2.5 wt % of Gelest TM-L01 limonenyltrisiloxane was added to improve combability and to improve feel.

Synthesis Example 11

Example 1 was repeated, except that 5 wt % of Gelest DE-15 polydiethylsiloxane, a low molecular weight siloxane, and 2.5 wt % of Gelest TM-L01 limonenyltrisiloxane were added to reduce "tack" and improve combability.

Synthesis Example 12

This Example is similar to that of Example 1 but is a higher solids version that uses maleic anhydride instead of acetic acid. According to the method of Example 1, the following components were added: 1700 mL deionized water, 13.4 g maleic anhydride, 320 mL propyltriethoxysilane, and 130 mL SM2159, but the hydroxyethylmethacrylate was not added. The resulting material was a cloudy liquid with a pH between 2 and 3.

Synthesis Example 13

This Example is similar to that of Example 1 but is a higher solids version that uses maleic anhydride instead of acetic acid. According to the method of Example 1, the following components were added: 1700 mL deionized water, 13.4 g maleic anhydride, 320 mL propyltriethoxysilane, 160 mL 1M 1 M NaHCO$_3$, and 130 mL SM2159, but the hydroxyethylmethacrylate was not added. The resulting material was a cloudy liquid with a pH between 5 and 8 which formed a film when applied to the skin and allowed to dry.

Application Example C

The composition of Example 1 was applied to a yellow pine board substrate by spray deposition by introducing the composition into a venturi sprayer with a 20:1 dilution. After drying overnight, the wood exhibited hydrophobic behavior, as evidenced by the contact angle of water drops exceeding 90°. The board substrate was subjected to a continuous spray of water and compared to a commercial water-sealant which contained aluminum hydroxystearate. The treatment with the composition of Example 1 continued to exhibit hydrophobic behavior for greater than two months, compared to less than six hours for the aluminum hydroxystearate control. In a separate experiment, the product of Example 1 was stored at ambient temperature for >2 years. When applied to yellow pine board under similar conditions, the same result was obtained.

We claim:

1. A stabilized mixture comprising an alkyltrialkoxysilane hydrolysate solution, an amine functional silicone emulsion, and a polyalkylsiloxane fluid,
   wherein the solution comprises alkylsilane triols and low molecular weight condensation products thereof having two to three silicon atoms.

2. The mixture according to claim 1, wherein the alkyl group in the alkyltrialkoxysilane contains about one to ten carbon atoms.

3. The mixture according to claim 2, wherein the alkyl group contains about two to eight carbon atoms.

4. The mixture according to claim 1, wherein the alkoxy group in the alkyltrialkoxysilane contains about one to four carbon atoms.

5. The mixture according to claim 1, wherein the silicone emulsion contains a high molecular weight amine functional polysiloxane containing alkoxy groups.

6. The mixture according to claim 1, wherein the polyalkylsiloxane is selected from polymethylethylsiloxane and polydiethylsiloxane.

7. The mixture according to claim 1, wherein the amine comprises an aminopropyl or aminoethylaminopropyl substitution.

8. A method of preparing the mixture according to claim 1, comprising hydrolyzing an alkoxysilane to form an aqueous solution comprising alkylsilanetriols and/or oligomeric alkylsilanetriol condensates; and stabilizing the solution by adding an amine functional silicone.

9. The method according to claim 8, wherein byproduct alcohols are optionally removed from the solution.

10. The mixture according to claim 1, further comprising a silanol-terminated diphenyl siloxane-dimethylsiloxane copolymer.

11. The mixture according to claim 1, wherein the mixture contains phenethylsilanetriol.

12. The mixture according to claim 1, wherein the mixture contains at least two different silanetriols.

13. A masonry treatment product comprising the stabilized mixture according to claim 1.

14. A cellulosic or wood treatment product comprising the mixture according to claim 1.

15. A hair care treatment product comprising the mixture according to claim 1.

16. A method of waterproofing a masonry object comprising applying the mixture according to claim 1 to the object.

17. A method of waterproofing a cellulosic or wood object comprising applying the mixture according to claim 1 to the object.

18. A method of improving sensory characteristics of hair comprising applying the mixture according to claim 1 to the hair, wherein the sensory characteristics include at least one of shine, feel, and combability.

* * * * *